United States Patent
Qu et al.

(10) Patent No.: US 8,077,953 B2
(45) Date of Patent: Dec. 13, 2011

(54) SYSTEM AND METHOD FOR AUTOMATIC DETECTION OF END OF DIASTOLE AND END OF SYSTOLE IMAGE FRAMES IN X-RAY VENTRICULAR ANGIOGRAPHY

(75) Inventors: Wei Qu, Schaumburg, IL (US); Sukhveer Singh, Algonquin, IL (US); Michael J. Keller, Algonquin, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 982 days.

(21) Appl. No.: 12/026,145

(22) Filed: Feb. 5, 2008

(65) Prior Publication Data

US 2009/0028412 A1    Jan. 29, 2009

Related U.S. Application Data

(60) Provisional application No. 60/952,386, filed on Jul. 27, 2007.

(51) Int. Cl.
*G06K 9/00* (2006.01)
(52) U.S. Cl. ........................................ 382/130; 382/132
(58) Field of Classification Search .................. 382/128, 382/130, 132, 168; 345/420
See application file for complete search history.

(56) References Cited

U.S. PATENT DOCUMENTS 6,045,512 A    4/2000    Roteliuk et al.

OTHER PUBLICATIONS

Oost et al., "Automated Contour Detection in X-Ray Left Ventricular Angiograms Using Multiview Active Appearance Models and Dynamic Programming", IEEE Transactions on Medical Imaging 25, pp. 1158-1171, Sep. 2006.
Arulampalam et al., "A Tutorial on Particle Filters for Online Nonlinear/Non-Gaussian Bayesian Tracking", IEEE Trans. Signal Processing 50, pp. 174-188, Feb. 2002.

*Primary Examiner* — Jurie Yun
(74) *Attorney, Agent, or Firm* — Alexander J Burke

(57) ABSTRACT

End-diastolic and end-systolic image frames are automatically selected on a real-time basis from a sequence of X-ray ventricular angiogram images by modeling the angiogram images by a dynamic graphical model and estimating a posterior probability density of the ventricular area in each angiogram image frame using Bayesian probability density propagation and adaptive background modeling. Then, a variation curve plot of expectation values of the posterior probability density of the ventricular area of each angiogram image frame is generated in which peaks and valleys in the variation curve correspond to end-diastolic and end-systolic angiogram image frames, respectively.

8 Claims, 6 Drawing Sheets

SYSTEM AND METHOD FOR AUTOMATIC DETECTION OF END OF DIASTOLE AND END OF SYSTOLE IMAGE FRAMES IN X-RAY VENTRICULAR ANGIOGRAPHY

RELATED APPLICATIONS

This application claims the benefit of U.S. Provisional Application Ser. No. 60/952,386 filed on Jul. 27, 2007, the entire disclosure of which is incorporated herein by reference.

FIELD

The disclosure relates to cardiac analysis. More particularly, the disclosure relates to a system and method for automatically selecting the end-diastolic and end-systolic image frames from an X-ray ventricular angiographic image sequence for cardiac analysis.

BACKGROUND

The heart contracts and relaxes with each heartbeat cycle. During contraction (systole), the heart ejects blood from the two ventricles. During relaxation (diastole), the ventricles refill with blood. Not all of the blood is emptied from the ventricles during systole. End of systole (ES) refers to the volume of blood remaining in the ventricles immediately after systole and before the beginning of diastole whereas ejection fraction refers to the percentage of blood which is pumped out of a filled ventricle during systole. End of diastole (ED) refers to the volume of blood held in the ventricles at the end of the refilling cycle.

X-ray left ventricular angiography is widely used for the assessment of cardiac functions by determining such parameters as ejection fraction, ED and ES. During this clinical check, patients undergo a cardiac catheterization procedure where X-ray opaque contrast dye is injected into left ventricle in order to visualize the left ventricle. The average acquisition time for the X-ray angiogram images is usually around 7 to 10 seconds, generating an X-ray image sequence with 150 to 400 frames.

In order to analyze the clinical parameters, an end-diastolic (ED) frame where the left ventricle is fully filled and an end-systolic (ES) frame where the left ventricle is maximally contracted have to be selected from the X-ray image sequence. After that, endocardial contours are segmented manually or automatically to determine the cross-sectional area of the projected left ventricle in the X-ray image frames, from which the ventricular volume in ED and ES can be estimated. The accuracy of the calculated ventricular volume depends on the accuracy of the ED and ES X-ray image frame selection.

Conventionally, ED and ES X-ray image frames are manually selected as the frames depicting the largest and smallest left ventricular area, respectively. This manual selection process is not only time consuming but also subject to human errors in visually selecting determining the ED and ES X-ray image frames. Automatic ED and ES frame selection is, thus, desirable for its potential to save clinicians' time and increase the selection accuracy.

However, because X-ray left ventricular images generally exhibit low contrast, noisy background, and dramatically changing left ventricular shape, accurate and dependable automatic method of selecting ED and ES frames has been elusive. The early efforts of computer aided left ventricular analysis has mainly focused on the contour segmentation of the X-ray images rather than ED and ES frame selection.

Many approaches have been studied in the literature. Some have proposed an approach to the automated segmentation of X-ray left ventricular angiograms based on active appearance models and dynamic programming. Others have presented an algorithm for automated detection of the left ventricular's typical behaviors in cardiac radionuclide angiographs. These methods do not involve ED and ES image frame selection because of the difficulties in X-ray left ventricular image sequences as mentioned above.

Recently, developments have been made in ECG gated ED and ES frame selection to circumvent the severe image ambiguities in X-ray angiography by synchronizing the ECG signal with the X-ray image data. Such ECG gated methods, however, are not robust because unlike in a healthy patient, when a patient's ECG is pathological, it is difficult to indicate the correct ED and ES frames because the QR and T waves of the ECG signal do not have good correspondence with ED and ES. This fact greatly limits the application of such ECG-based approach as most patients undergoing left ventricular angiography have irregular ECG signal. Moreover, since such kind of approaches require strict synchronization between the ECG signal and the X-ray image data, the record delay or noise may introduce additional error and lead to wrong detection results. Accordingly, there is a need for an improved system and method for finding ED and ES frames in an angiography series.

SUMMARY

The present disclosure describes a model-based Bayesian framework for automatic ED and ES image frame selection using only X-ray angiogram image sequence is disclosed. The X-ray angiogram is formulated by a dynamical graphical model. Then the posterior probability density of the left ventricular state is estimated by using Bayesian probability density propagation and adaptive background modeling. Compared to the manual ED and ES frame selection methods, the method of the present disclosure is more efficient, more accurate and robust. Compared to the ECG gated method, it avoids the signal synchronization issue and circumvents the difficulties inherent in the irregular ECG signals. Thus it is more practical and can be used much more widely.

According to an embodiment of the present disclosure, a computer implemented method of identifying and selecting end-diastolic and end-systolic X-ray image frames from a sequence of X-ray ventricular angiogram image frames is disclosed. The method comprises modeling the angiogram image frames by a dynamic graphical model where the dynamic graphical model formulates the areas of ventricular region in the angiogram image frames as a sequence of foreground states and formulates the backgrounds in the angiogram image frames as a sequence of background states. The changes of the foreground states and the background states from one image frame to a subsequent image frame is formulated as a Markov chain. The foreground states and the background states generate corresponding observations that are overlapped in each angiogram image frames. Next, the method estimates a posterior probability density of the foreground state of each angiogram image frame based on both foreground and background observations using Bayesian probability density propagation and adaptive background modeling. Then, an expectation value of the posterior probability density of the foreground state of each angiogram image fame is calculated wherein the expectation value represents an estimation of the area of the ventricular region represented in each angiogram image frame. A variation curve of the expectation values is then generated, the variation curve containing a plurality of peaks and valleys. The peaks correspond to end-diastolic angiogram image frames and the valleys correspond to end-systolic angiogram image frames. Thus, the method of the present disclosure allows selection of the ED and ES frames only based on the X-ray image sequence itself.

DETAILED DESCRIPTION

Figure 1:
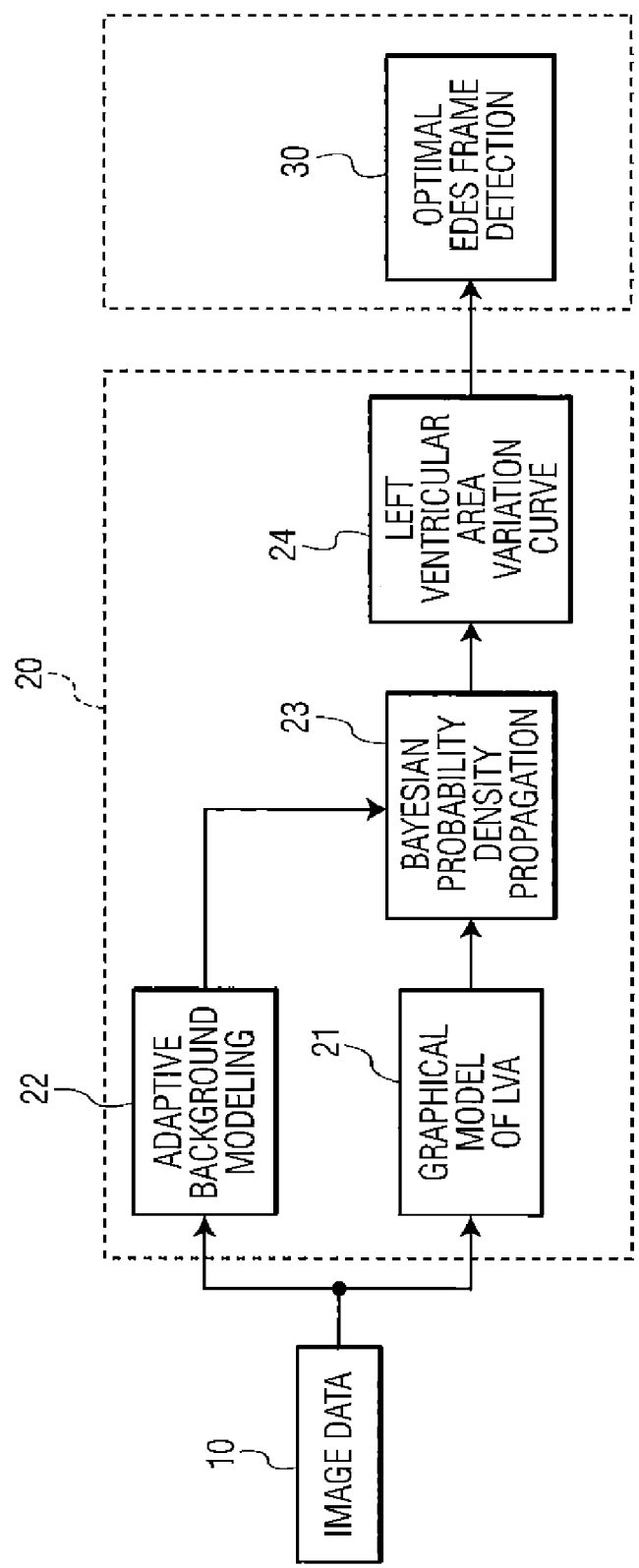
FIG. 1 is a block diagram of the method of the present disclosure.

According to an embodiment, a model-based Bayesian framework for ED and ES frame selection in left ventricular angiography image sequence will be described in detail. Referring to FIG. 1, left ventricular angiography image sequence data stream 10 is processed by the model-based Bayesian framework analysis 20 of the present disclosure and optimal ED and ES image frames are selected 30. The model-based Bayesian framework analysis 20 comprises the following main components: dynamic graphical modeling of the left ventricular area (LVA) in the image sequence 21; adaptive background modeling of the background in the image sequence 22; Bayesian probability density propagation 23; and generation of the LVA variation curve 24.

Graphical Analysis of X-Ray Left Ventricular Angiography

Figure 2A:
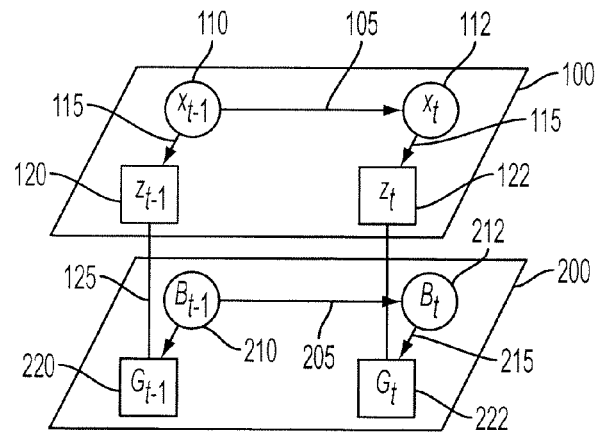
FIG. 2A-2C illustrate the dynamic graphical model of the left ventricle area (LVA) in the X-ray left ventricular angiogram image frames.

FIG. 2A illustrates the dynamic graphical model of the X-ray left ventricular angiogram image frames using two consecutive image frames as examples. The graphical model has two layers: a top layer 100 models the foreground in each image frame; a bottom layer 200 models the background in each frame. Foreground refers to the left ventricular region which will be observed in the image frame when the dye is introduced into the blood entering the left ventricle. In the graphical model, foreground states $\chi_t$ and $\chi_{t-1}$ represents the area of the left ventricular region in two consecutive image frames and are illustrated by the nodes 112 and 110, respectively. "t" is the time index. The method of the present disclosure treats the consecutive foregrounds states as having Morkov property. In other words, the conditional probability distribution of future foreground states, given the present foreground state and all past foreground states, depends only upon the present foreground state and not on any of the past foreground states. Therefore, the directed link 105 between the consecutive foreground states $\chi_t$ 112 and $\chi_{t-1}$ 110 represents the state transition density which is a Markov chain.

The nodes 120 and 122 in the foreground 100 represent the observations $z_t$ and $z-1_t$ (i.e. the X-ray angiogram images) associated with each foreground states $\chi_t$ 112 and $\chi_{t-1}$ 110, respectively. The directed links 115 from the foreground states $\chi_t$ 112 and $\chi_{t-1}$ 110 to their observations $z_t$ and $z-1_t$ represent the "generative" relationship and can be characterized by the local observation likelihood $p(z|\chi)$.

In the background layer 200, the nodes 212 and 210 represent the background states $B_t$ and $B_{t-1}$, respectively, at each time t and t−1. The background states represent everything in the image frames other than the ventricle areas (i.e. the foreground states). Because the background is not static but constantly changing due to the patient's chest movement, the directed link 215 between the two consecutive background states $B_t$ 212 and $B_{t-1}$ 210 represent the dynamics.

Similar to the foreground states, the background chest states $B_t$ and $B_{t-1}$ also "generate" observations $G_t$ and $G_{t-1}$, respectively, which are represented by the nodes 222 and 220 in the background layer 200. In each image frame, the foreground observation is overlapped with the background observation. The undirected link 125 between the foreground observation node and the background observation node in each frame reflects such kind of correlation.

Figure 2B:
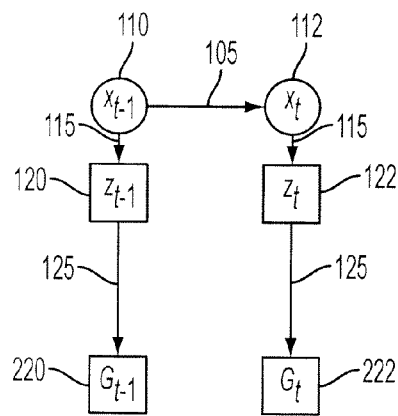
Figure 2C:
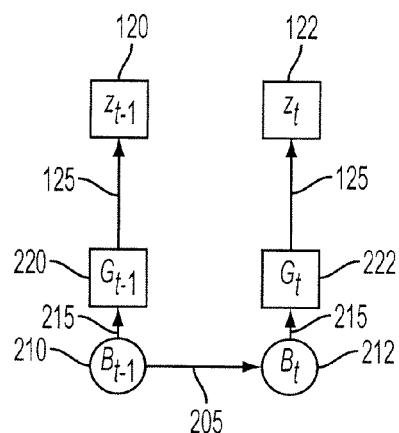

The graphical model of FIG. 2A can be further decomposed by using the following rules: (1) each undirected link 125 between foreground observation and background observation is decomposed into two directed links. The direction is from the analyzed layer to the other layer's observation; (2) only the directly linked observation nodes are retained in the decomposed model. The direct link here means whether a node is linked directly with the other layer. For example, when the foreground model is considered, the background state nodes B are removed since they are not directly linked with the nodes in foreground layer. All other nodes and links are neglected. FIGS. 2B and 2C show the decomposed results for the foreground layer 100 and the background layer 200, respectively. The links between the foreground observations and the background observations are now directed links with the directions specified by the above-stated rules. The two decomposed models, when used together simultaneously, retain all information from the original graphical model since all nodes and links are kept. The effectiveness of this simplification has been demonstrated by the inventors' experiments. The decomposed graphs are all Directed Acyclic Independent Graphs, which are directed graphs with non directed cycles used for the analysis and modeling in computer sciences and mathematics. By exploiting the Separation Theorem, which states the criterion to determine the conditional independence property in graph theory, the following Markov Properties of the decomposed graphs are obtained:

$$p(\chi_t, z_t, G_t | \chi_{1:t-1}, z_{1:t-1}, G_{1:t-1}) = p(\chi_t, z_t, G_t | \chi_{t-1}); \quad (p1)$$

$$p(z_t, G_t | \chi_t, \chi_{t-1}) = p(z_t, G_t | \chi_t); \quad (p2)$$

$$p(B_t | B_{1:t-1}, z_{1:t-1}, G_{1:t-1}) = p(B_t | B_{t-1}); \quad (p3)$$

$$p(z_t, G_t | B_{1:t}, z_{1:t-1}, G_{1:t-1}) = p(z_t, G_t | B_t) \quad (p4)$$

Next, derivation of the Bayesian probability density propagation rules to formulate both foreground and background models will be described. The goal is to estimate the posterior probability density of the foreground state $\chi$ based on both the foreground and background observations $p(\chi_{1:t} | z_{1:t}, G_{1:t})$, where $\chi_{1:t}$ is the set of all foreground states up to time t; $z_{1:t}$ is the set of all foreground observations up to time t; and $G_{1:t}$ is the set of all background observations up to time t. After the posterior probability density $p(\chi_{1:t}|z_{1:t}, G_{1:t})$ is estimated, the expectation value $E_t(\hat{x}_{1:t})$ which reflects the area variation of the left ventricular region. By using Bayes' rule, we have $$p(x_{1:t} | z_{1:t}, G_{1:t}) = \frac{p(x_t, z_t, G_t | x_{1:t-1}, z_{1:t-1}, G_{1:t-1})}{p(z_{1:t}, G_{1:t})} \quad (1)$$

$$p(x_{1:t-1}, z_{1:t-1}, G_{1:t-1})$$

$$= \frac{p(x_t, z_t, G_t | x_{t-1})}{p(z_t, G_t | z_{1:t-1}, G_{1:t-1})}$$

$$p(x_{1:t-1} | z_{1:t-1}, G_{1:t-1})$$

$$= \frac{p(z_t, G_t | x_t, x_{t-1})p(x_t | x_{t-1})}{p(z_t, G_t | z_{1:t-1}, G_{1:t-1})} \quad (2)$$

$$p(x_{1:t-1} | z_{1:t-1}, G_{1:t-1})$$

$$= \frac{p(z_t, G_t | x_t)p(x_t | x_{t-1})}{p(z_t, G_t | z_{1:t-1}, G_{1:t-1})}$$

$$p(x_{1:t-1} | z_{1:t-1}, G_{1:t-1}).$$

In (1), the Markov property (p1) is applied. In (2), the Markov property (p2) is applied. $p(\chi_t|\chi_{t-1})$ is the foreground state transition density. $p(\chi_{1:t-1}|z_{1:t-1}, G_{1:t-1})$ is the posterior probability density in the previous step. The probability density $p(z_t, G_t|\chi_t)$ in (2) is a model-based likelihood since it exploits the background model information, which is discussed in detail below.

The Bayesian probability density propagation rule derived above can be implemented by different methods such as kernel density estimation. In one example of this disclosure, a sequential Monte Carlo simulation method is used to estimate the probability density propagation. Specifically, the posterior probability density of the foreground state $p(\chi_{1:t}|z_{1:t}, G_{1:t})$ is approximated as $$p(x_{1:t} | z_{1:t}, G_{1:t}) \approx \sum_{n=1}^{N} w_t^n \delta(x_{1:t} - x_{1:t}^n), \quad (3)$$

where $\{x_{1:t}^n, n=1 \ldots N\}$ is a set of samples (i.e. a set of generated foreground states), $\{w_t^n, n=1 \ldots N\}$ are the associated weights, and $\delta$ is the Dirac delta function. Based on importance sampling theory, when the samples are obtained from an importance density $q(\cdot)$, the can be given by $$w_t^n \propto \frac{p(x_{1:t}^n | z_{1:t}, G_{1:t})}{q(x_{1:t}^n | z_{1:t}, G_{1:t})} \quad (4)$$

Moreover, if an importance density is chosen which can be factorized as $$q(x_{1:t}|z_{1:t},G_{1:t})=q(x_t|x_{1:t-1},z_{1:t},G_{1:t})q(x_{1:t-1}|z_{1:t-1},G_{1:t-1}), \quad (5)$$

and substitute (3) into (4), the weights become $$w_t^n \propto \frac{p(z_t, G_t | x_t^n)p(x_t^n | x_{t-1}^n)p(x_{1:t-1}^n | z_{1:t-1}, G_{1:t-1})}{q(x_t^n | x_{1:t-1}^n, z_{1:t}, G_{1:t})q(x_{1:t-1}^n | z_{1:t-1}, G_{1:t-1})} = \quad (6)$$

$$\frac{p(z_t, G_t | x_t^n)p(x_t^n | x_{t-1}^n)}{q(x_t^n | x_{1:t-1}^n, z_{1:t}, G_{1:t})} w_{t-1}^n.$$

(6) provides the weights an updated rule. Furthermore, if the samples from $p(\chi_t|\chi_{t-1})$ namely, selecting $q(\chi_t|\chi_{1:t}, z_{1:t}, G_{1:t})=p(\chi_t|\chi_{t-1})$, then the weight update rule is simplified into $$w_t^n \propto p(z_t, G_t|x_t^n)w_{t-1}^n. \quad (7)$$

In (7), probability density $p(z_t, G_t|x_t^n)$ is the model-based likelihood.

Because the attributes of X-ray angiogram images are not optimal for estimating such observation in computer vision, the method of the present disclosure utilizes kernel-based histogram to represent both the foreground observation $z_t$ and the background observation $G_t$. Specifically, the kernel-based histograms for foreground observation $z_t$ and background observation $G_t$ are defined as $h(z_t)$ and $h(G_t)$, respectively. Since the foreground observation $z_t$ and the background observation $G_t$ are overlapped together in one image frame, in order to distinguish them from each other, the method of the present disclosure calculates the background prediction $p(B_{1:t}|z_{1:t-1}, G_{1:t-1})$ first, and then use it to estimate the background observation $G_t$. Thus, we get $$p(B_{1:t}|z_{1:t-1},G_{1:t-1}) \propto p(B_t|B_{1:t-1},z_{1:t-1},G_{1:t-1})$$
$$p(B_{1:t-1}|z_{1:t-1},G_{1:t-1})=p(B_t|B_{t-1})p(B_{1:t-1}|z_{1:t-1},G_{1:t-1}) \quad (8)$$

where Markov property (p3) is applied. In (8), $p(B_t|B_{t-1})$ is the background dynamics, and $p(B_{1:t-1}|z_{1:t-1}, G_{1:t-1})$ is the posterior density of background state at time t−1.

Having the predication $p(B_{1:t-1}|z_{1:t-1}, G_{1:t-1})$ at time t, the background model can be (8) further adaptively updated as follows $$p(B_{1:t} | z_{1:t}, G_{1:t}) = \quad (9)$$

$$\frac{p(z_t, G_t | B_{1:t}, z_{1:t-1}, G_{1:t-1})p(B_{1:t}, z_{1:t-1}, G_{1:t-1})}{p(z_{1:t}, G_{1:t})} =$$

$$\frac{p(z_t, G_t | B_t)p(B_{1:t} | z_{1:t-1}, G_{1:t-1})}{p(z_t, G_t | z_{1:t-1}, G_{1:t-1})}.$$

where in (9), Markov property (p4) is applied.

The expectation of $p(B_{1:t}|z_{1:t-1}, G_{1:t-1})$ can give an estimation of the observation $G_t$. After that, the model-based likelihood is further modeled as $$p(z_t, G_t | x_t) = \frac{1}{2\pi\sigma} \exp\left\{-\frac{\left[x_t - \int f(\hbar_i(z_t) - \hbar_i(G_t))\right]^2}{\sigma^2}\right\}, \quad (10)$$

where $$f(\cdot) = \begin{cases} 1, & \hbar_i(z_t) > \hbar_i(G_t), \\ 0, & \hbar_i(z_t) \leq \hbar_i(G_t), \end{cases} \quad (11)$$

i is the index of bins in the histogram and $\sigma$ is a variance parameter.

Figure 3:
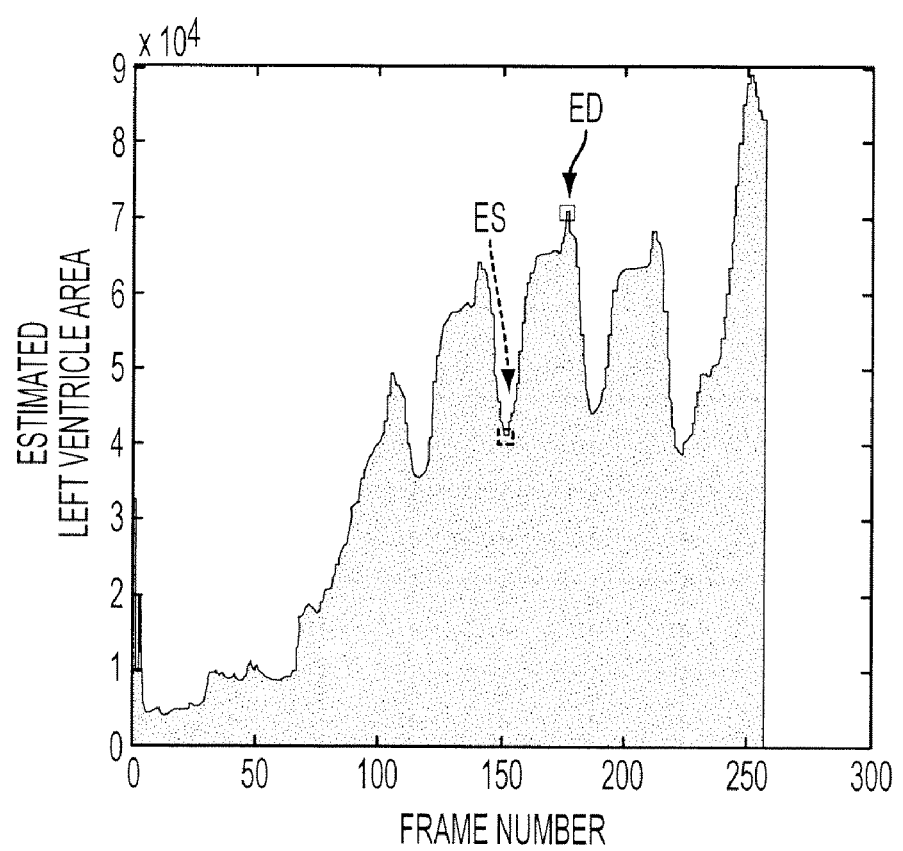
FIG. 3 is an example of a left ventricle area variation curve.

After the posterior probability density $p(\chi_{1:t}|z_{1:t}, G_{1:t})$ is calculated, its expectation $E_t(\hat{x}_{1:t})$ gives a variation curve of the left ventricle's area. FIG. 3 is an example of such a variation curve 300. In the variation curve plot, the X-axis represents the angiogram image frames and the y-axis represents the estimated expected value of the posterior probability density. The variation curve will exhibit multiple pairs of peaks and valleys, peaks 320 corresponding to the ED frames in which left ventricle has the maximal size while the valleys 310 correspond to the ES frames where the left ventricle has the minimal size.

Since the X-ray opaque dye is usually injected after about the first 30 frames of the X-ray angiogram session, these initial frames can be ignored and detect the ED and ES frames from the rest of the variation curve. Different signal processing techniques can be used to further find the ED and ES frames from the variation curve. For example, a band-pass filter was used to remove the noise and then detect the zero crossings on the second derivative of the density curve. After that, intuitive rules can be applied to determine the optimal ED and ES pair among the plurality of peaks and valleys in the variation curve. For example, if there were concerns that the first one or two heart beats immediately following the injection of the opaque dye into the left ventricle might be affected by the presence of the dye, the method of the present disclosure can be configured to always ignore the first two peaks in the left ventricle area variation curve and select the optimal ED and ES pair from the remainder of the peaks.

In one embodiment of the computer system that implements the method of the present disclosure the left ventricle area variation curve is displayed on the computer system's display unit for the operator's viewing. The optimal ED and ES frame pairs also would be displayed on the display unit along with the variation curve. The computer system can be configured to give the operator the option of viewing the ED and ES frames associated with other peaks shown in the variation curve.

EXAMPLE

To examine the effectiveness of the methodology, the method was tested on a clinical data set including 21 X-ray left ventricular angiogram image sequences. All of them were acquired in 30° right anterior oblique view, using a standard contrast agent. The average acquisition time was about 7 to 10 seconds covering 5 to 8 cardiac cycles. The data includes both adult and child patients suffering from one, two or diffuse coronary diseases. The ED and ES frame pair in each angiogram sequence was manually determined by experts in order to evaluate the accuracy of the method of the present disclosure.

The experiments were performed using Matlab, a numerical computing environment and programming language, on a laptop computer with 2.33 GHz Intel Core™ 2 CPU and 2 G RAM. Without code optimization, the method detected the ED and ES frames within 1.5 to 4.5 seconds for sequences having 150 to 400 image frames. The average success rate was 97% for ED and 94% for ES frames.

Figure 4A:
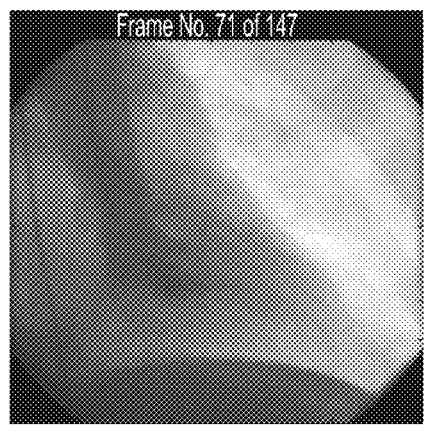
FIGS. 4A and 4B are optimal ES and ED image frame pair selected by the method of the present disclosure from an X-ray left ventricle angiogram sequence.
Figure 4B:
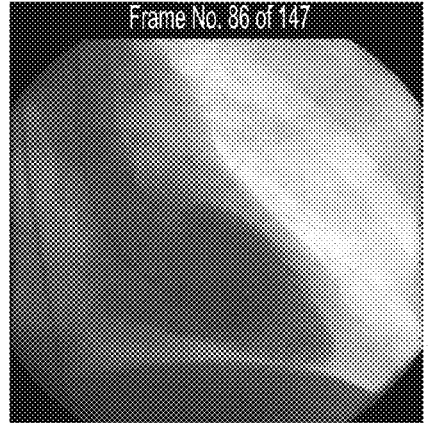
Figure 4C:
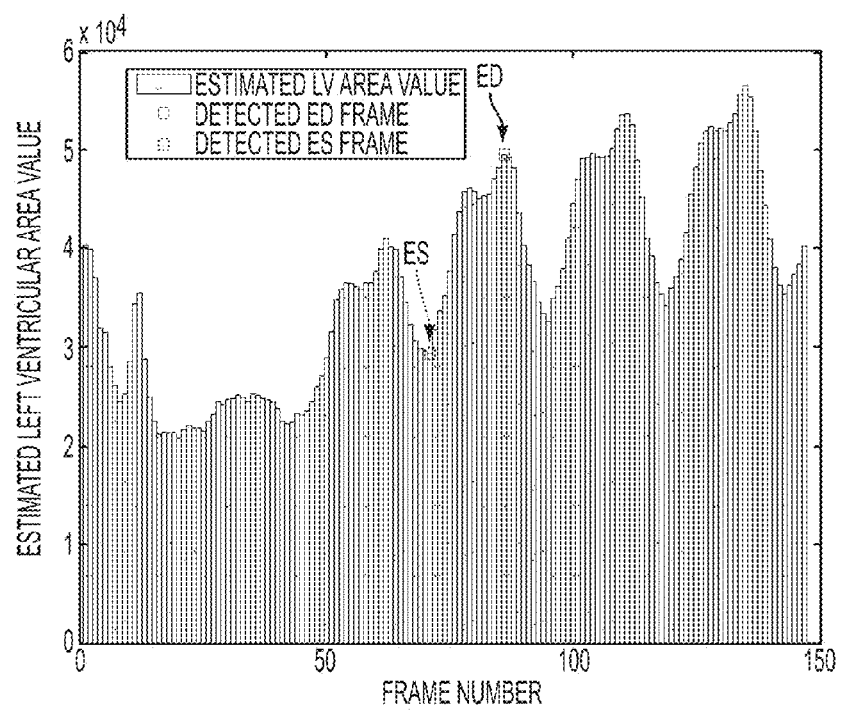
FIG. 4C is the left ventricle area variation curve generated by the method of the present disclosure from the X-ray left ventricle angiogram sequence corresponding to the ES and ED image frames of FIGS. 4A and 4B.
Figure 5A:
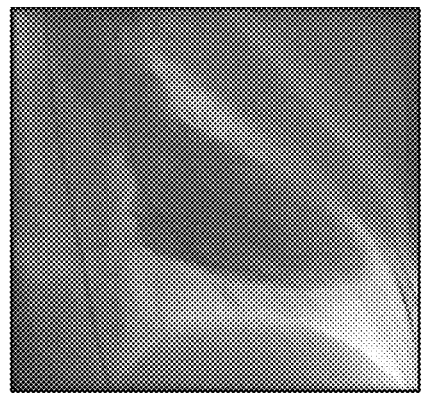
FIGS. 5A and 5B are optimal ES and ED image frame pair selected by the method of the present disclosure from another X-ray left ventricle angiogram sequence.
Figure 5B:
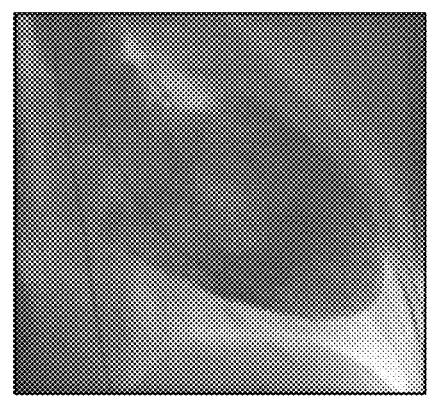
Figure 5C:
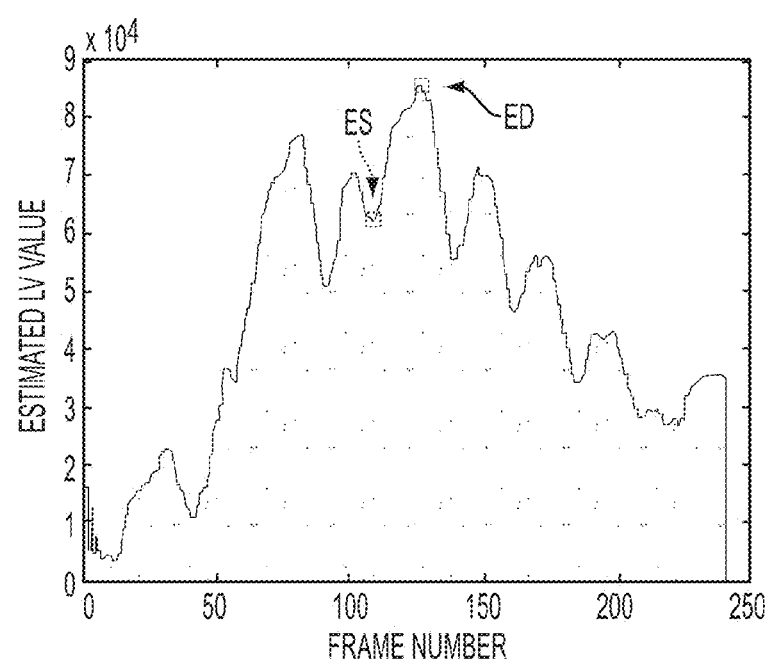
FIG. 5C is the left ventricle area variation curve generated by the method of the present disclosure from the X-ray left ventricle angiogram sequence corresponding to the ES and ED image frames of FIGS. 5A and 5B.

FIGS. 4 and 5 illustrate the experimental results for two sequences where FIGS. 4A and 5A are the selected optimal ES frames; FIGS. 4B and 5B are the selected optimal ED frames; and FIGS. 4C and 5C show the estimated left ventricular area variation curves in which the peaks and valleys corresponding to the optimal ED and ES frames are identified.

Even for the angiographical sequences with a lot of noise, uneven distributed contrast, and non-static background, the method of the present disclosure can achieve robust optimal selection of both ED and ES image frames. Moreover, the estimated left ventricle variation curve reflects many additional useful information. For example, it clearly shows how many cardiac cycles appeared during the acquisition; when the contrast dye was injected into the left ventricle and faded away (the peaks and valleys appear in the variation curve after the contrast dye is injected and they disappear after the contrast dye fades away); the heart rate; and whether the heart motion was regular, etc. These types of information are not limited to ED/ES frame selection but can also be used to facilitate other left ventricular analysis.

Figure 6:
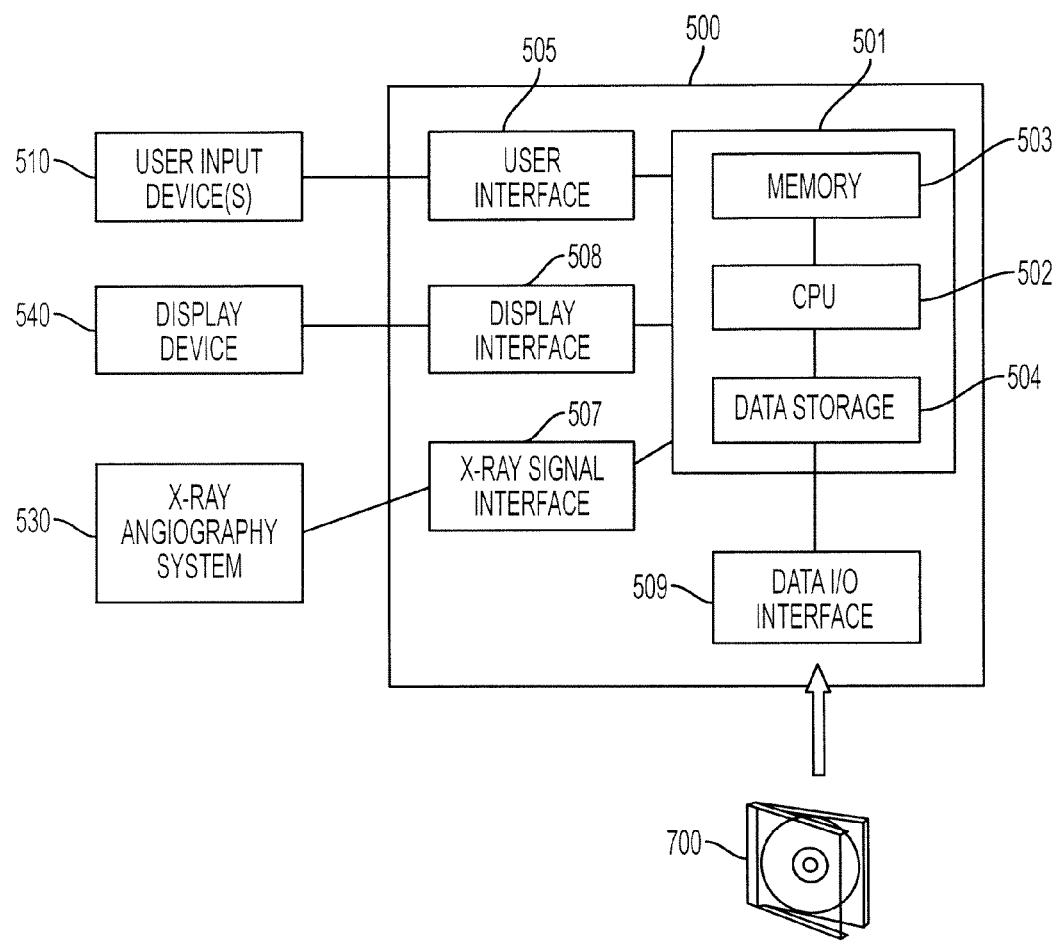
FIG. 6 is a block diagram of an exemplary embodiment of a system for implementing the method of the present disclosure.

FIG. 6 shows a block diagram of an exemplary embodiment of a system for implementing the method of the present disclosure. The system 500 includes a computer 501 operably connected and in data communication with a user input/output (I/O) interface 505, an X-ray image signal interface 507, a display interface 508. The computer 501 can also include a central processing unit (CPU) 502, a memory unit 503, and a program/data storage unit 504. The system 500 can further comprise external peripheral devices and sub-systems including one or more user input devices 510, a digital X-ray sub-system 530, and a display device 540.

The method of the present disclosure can be implemented in the system 500 by installing a computer program code embodying the algorithms of the method disclosed herein into the computer 501, thereby allowing the system 500 to perform the automated process of selecting the optimal ED and ES image frames from a sequence of X-ray left ventricular angiogram image frames provided to the system 500 via the X-ray image signal interface 507. The computer program code can be provided as a software in a portable data storage media 700 such as random access memory (RAM) devices, read only memory (ROM) devices, EPROMs, EEPROMs, compact disks (CD), DVDs, flash memory devices, magnetic disks, optical disks, etc. and loaded on to the system's computer 501 via the data I/O interface 509 and in to the program/data storage unit 504. The computer program code can also be preloaded into the internal memory unit 503 or the program/data storage unit 504 as a firmware. The selected ED and ES image frames and the left ventricular area variation curve can be displayed on the display device 540.

The present disclosure may be embodied in other specific forms without departing from the spirit or essential attributes of the disclosure. Accordingly, reference should be made to the appended claims, rather than the foregoing specification, as indicating the scope of the invention. Although the foregoing description is directed to exemplary embodiments, it is noted that other variations and modification will be apparent to those skilled in the art, and may be made without departing from the spirit or scope of the invention. The appended claims should be construed broadly to encompass other variants and embodiments that may be constructed by those of ordinary skill in the art within the scope and range of equivalents of the invention.

What is claimed is:

1. A computer implemented method of identifying and selecting end-diastolic and end-systolic X-ray image frames from a sequence of X-ray ventricular angiogram image frames, the method comprising:
   employing at least one computer for,
      modeling said angiogram image frames by a dynamic graphical model, said dynamic graphical model formulating areas of ventricular region in the angiogram image frames as a sequence of foreground states, formulating backgrounds in the angiogram image frames as a sequence of background states, wherein the changes of the foreground states and the background states from one image frame to a subsequent image frame is formulated as a Markov chain and the foreground states and the background states generating corresponding observations that are overlapped in each angiogram image frames;
      estimating a posterior probability density of the foreground state of each angiogram image frame based on both foreground and background observations using Bayesian probability density propagation and adaptive background modeling;

calculating an expectation value of said posterior probability density of the foreground state of each angiogram image frame, said expectation value representing an estimation of the area of the ventricular region represented in each angiogram image frame; and generating a variation curve of the expectation values, said variation curve containing a plurality of peaks and valleys whereby said peaks correspond to end-diastolic angiogram image frames and said valleys correspond to end-systolic angiogram image frames.

2. The method of claim 1 further comprising determining optimal end-diastolic and end-systolic angiogram image frame pairs from the variation curve of the expectation values.

3. The method of claim 1, wherein estimating a posterior probability density of the foreground state of each angiogram image frame based on both foreground and background observations using Bayesian probability density propagation and adaptive background modeling includes using sequential Monte Carlo simulation method to estimate the probability density propagation.

4. The method of claim 3, wherein the posterior probability density of the foreground state is expressed as $p(\chi_{1:t}|z_{1:t}, G_{1:t})$, where $\chi_t$ represents the area of the ventricular region in X-ray angiogram image frame at time index t, $z_t$ represents said foreground observation associated with the foreground state $\chi_t$ at time index t, and $G_t$ represents the background observation associated with the foreground state $\chi_t$ at time index t, and $p(\chi_{1:t}|z_{1:t}, G_{1:t})$ is approximated as $$p(x_{1:t}|z_{1:t}, G_{1:t}) \approx \sum_{n=1}^{N} w_t^n \delta(x_{1:t} - x_{1:t}^n),$$

where $\{x_{1:t}^n, n=1 \ldots N\}$ is a set of said samples of the foreground states, $\{w_t^n, n=1 \ldots N\}$ are the associated weights, and $\delta$ is the Dirac delta function, and based on importance sampling theory, when the samples are obtained from an importance density $q(\cdot)$, the weights are given by $$w_t^n \propto \frac{p(x_{1:t}^n|z_{1:t}, G_{1:t})}{q(x_{1:t}^n|z_{1:t}, G_{1:t})}.$$

5. A non-transitory computer readable program storage device, tangibly embodying a program of instructions executable by the computer to perform a method of identifying and selecting end-diastolic and end-systolic X-ray image frames from a sequence of X-ray ventricular angiogram image frames, wherein said method comprising:

modeling said angiogram image frames by a dynamic graphical model, said dynamic graphical model formulating areas of ventricular region in the angiogram image frames as a sequence of foreground states, formulating backgrounds in the angiogram image frames as a sequence of background states, wherein the changes of the foreground states and the background states from one image frame to a subsequent image frame is formulated as a Markov chain and the foreground states and the background states generating corresponding observations that are overlapped in each angiogram image frames;

estimating a posterior probability density of the foreground state of each angiogram image frame based on both foreground and background observations using Bayesian probability density propagation and adaptive background modeling;

calculating an expectation value of said posterior probability density of the foreground state of each angiogram image frame, said expectation value representing an estimation of the area of the ventricular region represented in each angiogram image frame; and generating a variation curve of the expectation values, said variation curve containing a plurality of peaks and valleys whereby said peaks correspond to end-diastolic angiogram image frames and said valleys correspond to end-systolic angiogram image frames.

6. The device of claim 5, wherein the method further comprising determining optimal end-diastolic and end-systolic angiogram image frame pairs from the variation curve of the expectation values.

7. The device of claim 5, wherein the estimating a posterior probability density of the foreground state of each angiogram image frame based on both foreground and background observations using Bayesian probability density propagation and adaptive background modeling step of the method further includes using sequential Monte Carlo simulation method to estimate the probability density propagation.

8. The device of claim 5, wherein the posterior probability density of the foreground state is expressed as $p(\chi_{1:t}|z_{1:t}, G_{1:t})$, where $\chi_t$ represents the area of the ventricular region in X-ray angiogram image frame at time index t, $z_t$ represents said foreground observation associated with the foreground state $\chi_t$ at time index t, and $G_t$ represents the background observation associated with the foreground state $\chi_t$ at time index t, and $p(\chi_{1:t}|z_{1:t}, G_{1:t})$ is approximated as $$p(x_{1:t}|z_{1:t}, G_{1:t}) \approx \sum_{n=1}^{N} w_t^n \delta(x_{1:t} - x_{1:t}^n),$$

where $\{x_{1:t}^n, n=1 \ldots N\}$ is a set of said samples of the foreground states, $\{w_t^n, n=1 \ldots N\}$ are the associated weights, and $\delta$ is the Dirac delta function, and based on importance sampling theory, when the samples are obtained from an importance density $q(\cdot)$, the weights are given by $$w_t^n \propto \frac{p(x_{1:t}^n|z_{1:t}, G_{1:t})}{q(x_{1:t}^n|z_{1:t}, G_{1:t})}.$$

* * * * *